(12) United States Patent
Krubasik et al.

(10) Patent No.: US 9,453,187 B2
(45) Date of Patent: Sep. 27, 2016

(54) DETERGENT COMPOSITION

(75) Inventors: Lucia Krubasik, Ludwigshafen (DE); Frank Dierkes, Ludwigshafen (DE); Steffen Lingler, Ludwigshafen (DE); Jörg Pflug, Ludwigshafen (DE)

(73) Assignee: RECKITT BENCKISER FINISH B.V., Hoofddorp (NL)

( * ) Notice: Subject to any disclaimer, the term of this patent is extended or adjusted under 35 U.S.C. 154(b) by 0 days.

(21) Appl. No.: 13/393,866

(22) PCT Filed: Sep. 6, 2010

(86) PCT No.: PCT/GB2010/051472
§ 371 (c)(1),
(2), (4) Date: Mar. 30, 2012

(87) PCT Pub. No.: WO2011/027170
PCT Pub. Date: Mar. 10, 2011

(65) Prior Publication Data
US 2012/0178148 A1 Jul. 12, 2012

(30) Foreign Application Priority Data
Sep. 7, 2009 (GB) .................. 0915572.2

(51) Int. Cl.
C12N 9/54 (2006.01)
C11D 3/386 (2006.01)
C11D 3/37 (2006.01)
C11D 3/33 (2006.01)
C11D 3/36 (2006.01)
C11D 3/39 (2006.01)

(52) U.S. Cl.
CPC ............. *C11D 3/386* (2013.01); *C11D 3/33* (2013.01); *C11D 3/361* (2013.01); *C11D 3/378* (2013.01); *C11D 3/3942* (2013.01); *C11D 3/3945* (2013.01); *C12N 9/54* (2013.01)

(58) Field of Classification Search
CPC .................................. C11D 3/386; C12N 9/54
See application file for complete search history.

(56) References Cited

U.S. PATENT DOCUMENTS

| | | | |
|---|---|---|---|
| 7,125,828 B2 * | 10/2006 | Catlin | B65B 9/04 510/220 |
| 7,259,134 B2 * | 8/2007 | Beckholt | B65D 85/808 510/220 |
| 7,449,187 B2 | 11/2008 | Weber et al. | |
| 8,163,686 B2 * | 4/2012 | Gibis | C11D 3/33 134/25.2 |
| 8,962,543 B2 * | 2/2015 | Lingler | C11D 3/2089 510/220 |
| 2003/0078179 A1 * | 4/2003 | Ghosh et al. | 510/392 |
| 2005/0181446 A1 * | 8/2005 | Roggen et al. | 435/7.1 |
| 2005/0227896 A1 * | 10/2005 | Speckmann | B65D 1/04 510/392 |
| 2005/0239043 A1 | 10/2005 | Harding | |
| 2005/0282725 A1 * | 12/2005 | Dasque et al. | 510/446 |
| 2006/0049077 A1 * | 3/2006 | Fregonese | C11D 3/3945 206/524.7 |
| 2006/0122088 A1 * | 6/2006 | Sadlowski | C11D 3/2075 510/295 |
| 2007/0054829 A1 * | 3/2007 | Gentschev | C11D 3/386 510/302 |
| 2009/0018043 A1 * | 1/2009 | Beckers | B30B 11/06 510/224 |
| 2009/0075855 A1 * | 3/2009 | Gibis | C11D 3/33 510/224 |
| 2009/0305934 A1 * | 12/2009 | Creamer et al. | 510/221 |
| 2009/0325840 A1 * | 12/2009 | Preuschen | C11D 3/046 510/221 |
| 2010/0152088 A1 * | 6/2010 | Estell et al. | 510/226 |
| 2010/0160202 A1 * | 6/2010 | Housmekerides | C11D 1/72 510/218 |
| 2010/0206013 A1 * | 8/2010 | Kotsakis | C11D 11/0017 68/9 |
| 2010/0292120 A1 * | 11/2010 | Oehms | C11D 3/33 510/224 |
| 2011/0017239 A1 * | 1/2011 | Vanloyen | C11D 3/3769 134/25.2 |
| 2011/0045571 A1 * | 2/2011 | Ferrari et al. | 435/221 |
| 2011/0281328 A1 * | 11/2011 | Estell et al. | 435/221 |
| 2012/0097193 A1 * | 4/2012 | Rossetto | C11D 3/39 134/25.2 |
| 2012/0234359 A1 * | 9/2012 | Krubasik | C11D 1/722 134/25.2 |

FOREIGN PATENT DOCUMENTS

EP 0571049 A1 11/1993
EP 2100947 A1 9/2009
(Continued)

OTHER PUBLICATIONS

International Search Report for application PCT/GB2010/051472 dated Mar. 15, 2011.
(Continued)

*Primary Examiner* — Nashaat Nashed
*Assistant Examiner* — William W Moore
(74) *Attorney, Agent, or Firm* — Troutman Sanders LLP; Ryan Schneider; Chris Davis

(57) ABSTRACT

A detergent composition comprising; a subtilisin variant having the amino acid sequence set forth in SEQ ID NO 1, and at least one additional ingredient selected from; i) bleaches selected from percarbonates, persulphates and organic peracids, ii) aminocarboxylates, or iii) sulphonated polymers, or iv) organophosphonic acids or salts thereof and mixtures thereof is provided. Also provided is a detergent composition comprising a subtilisin variant having the amino acid sequence set forth in SEQ ID NO 1, wherein, the detergent composition is at least partially enveloped in a water soluble or water dispersible package. The compositions exhibit good performance on proteinaceous stains, even when formulated at alkaline pHs. A method of removing proteinaceous stains from surfaces comprising such stains is also provided.

17 Claims, No Drawings

(56) References Cited

FOREIGN PATENT DOCUMENTS

| | | |
|---|---|---|
| JP | 2006513691 A | 4/2006 |
| WO | 9402618 A1 | 2/1994 |
| WO | 03072746 A2 | 9/2003 |
| WO | 2007052064 A1 | 5/2007 |
| WO | 2009040544 A1 | 4/2009 |
| WO | 2009098660 A1 | 8/2009 |
| WO | 2009102854 A1 | 8/2009 |
| WO | 2010056634 A1 | 5/2010 |

OTHER PUBLICATIONS

Methods for ascertaining the cleaning performance of dishwasher detergents (part A), SÖFW-Journal, vol. 125, Nov. 1999, pp. 53-59.
Methods for Ascertaining the Cleaning Performance of Dishwasher detergents (Part B, updated 2005), SÖFW-Journal, vol. 132, Aug. 2006, pp. 35-49.

\* cited by examiner

SEQUENCE LISTING

```
<160> NUMBER OF SEQ ID NOS: 1

<210> SEQ ID NO 1
<211> LENGTH: 269
<212> TYPE: PRT
<213> ORGANISM: Bacillus sp.

<400> SEQUENCE: 1

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60
```

```
His Val Ala Gly Thr Ile Ala Ala Leu Asn Asn Ser Ile Gly Val Leu
 65                  70                  75                  80

Gly Val Ala Pro Asn Ala Glu Leu Tyr Ala Val Lys Val Leu Gly Ala
                 85                  90                  95

Ser Gly Met Gly Ser Val Ser Ser Ile Ala Gln Gly Leu Glu Trp Ala
            100                 105                 110

Gly Asn Asn Val Met His Val Ala Asn Leu Ser Leu Gly Leu Gln Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

DETERGENT COMPOSITION

This is an application filed under 35 USC 371 of PCT/GB2010/051472.

TECHNICAL FIELD

The present invention relates to detergent compositions comprising subtilisin variants as the enzyme, in particular a *Bacillus* sp. subtilisin variant. In particular the present invention relates to such compositions to be used in automatic washing processes, such as automatic dishwashing processes.

BACKGROUND OF THE INVENTION

It is well known to use detergent compositions in applications such as laundry processes and automatic dishwashing.

In order to obtain good cleaning performance on proteinaceous stains, e.g. egg yolk, milk and meat stains, it is desirable to include a protease enzyme in detergent compositions to be used in laundry and dishwashing processes (especially automatic dishwashing applications). Such stains are not readily removed by bleaching agents or other types of enzymes but can make up a significant proportion of the stains encountered in laundry and dishwashing.

It is usual to formulate such laundry and automatic dishwashing detergent compositions at alkaline pHs to optimise the overall performance of these compositions. However, such alkaline pHs are generally unsuitable for protease enzymes resulting in poor performance and/or stability, or, they may require specialised protease enzymes to be formulated which are more effective in alkaline pHs but which often exhibit limited performance. Furthermore they may be difficult to formulate into a wide range of detergent product formats.

Accordingly there is a need in the art to provide laundry and dishwashing compositions (especially automatic dishwashing compositions) which show good efficacy on proteinaceous stains and in particular which compositions can be formulated at alkaline pHs whilst still exhibiting effective removal of such stains. There is also a need to provide such compositions which in addition which exhibit good performance on bleachable stains and/or provide good streak resistance in dishwashing applications.

It is an object of the present invention to address one or more of the above-mentioned problems.

In particular, it is an object of the present invention to provide laundry detergent compositions and dishwashing detergent compositions which are effective in the removal of proteinaceous stains. It is also an object of the present invention to provide such compositions which show good performance on bleachable stains and/or provide good filming and/or spotting resistance in dishwashing applications.

STATEMENT OF INVENTION

It has surprisingly been found that one or more of the above problems are addressed by the compositions of the present invention.

Thus according to a first aspect of the present invention there is provided a detergent composition comprising;
 a) A subtilisin variant having the amino acid sequence set forth in SEQ ID NO 1, and
 b) at least one additional ingredient selected from;
  i) bleaches selected from percarbonates, persulphates and organic peracids,
  ii) aminocarboxylates, or
  iii) sulphonated polymers, or
  iv) organophosphonic acids or salts thereof, and mixtures thereof.

Preferably the composition is laundry composition or a dishwashing composition and in particular an automatic dishwashing detergent composition.

It is preferred that the subtilisin variant having the amino acid sequence set forth in SEQ ID NO 1 is an isolated variant.

Preferably the percarbonate and persulphate bleach comprises sodium or potassium percarbonate or persulphate.

Preferably the organic peracids comprise perbenzoic and/or peroxycarboxylic acids. Preferably the peroxycarboxylic acids comprise monoperoxyphthalic acid, diperoxyphthalic acid, 2-octyldiperoxysuccinic acid, diperoxydodecanedicarboxylic acid, diperoxy-azelaic acid, imidoperoxycarboxylic acid or phthalimidoperhexanoic acid including derivatives and salts thereof and mixtures thereof. Especially preferred is phthalimidoperhexanoic acid (PAP) or derivatives or salts thereof.

It is preferred that the aminocarboxylate comprises methyl-glycine-diacetic acid, glutamic-N,N-diacetic acid, and salts or derivatives and mixtures thereof.

It is preferred that the sulphonated polymer comprises monomers of a carboxylic acid or a salt thereof and a sulphonated monomer, especially acrylic acid and/or 2-acrylamido-2-methyl-1-propanesulphonic acid (AMPS).

Preferably the organophosphonic acid comprises 1, hydroxy, ethylidene 1,1-diphosphonic acid (HEDP) or a salt thereof.

It is preferred that the compositions further comprise surfactant. It is most preferred that the automatic dishwashing compositions of the present invention comprise non-ionic surfactant.

According to a second aspect of the present invention there is provided a detergent composition comprising a subtilisin variant having the amino acid sequence set forth in SEQ ID NO 1, wherein, the detergent composition is at least partially enveloped in a water soluble or water dispersible package.

Preferably the packaging material used to produce the water soluble or water dispersible package is preferably polymeric and most preferably is selected from polyvinyl alcohol, celluloses and cellulose derivatives, starches, gelatine, polyglycolides, gelatine and polylactides copolymers or a mixture or co-polymer thereof.

It is preferred that the detergent composition is fully enveloped by the water soluble or water dispersible package. According to certain embodiments of the present invention it is preferred that the water soluble or water dispersible package has a plurality of compartments.

According to a third aspect of the invention there is provided a method of removing or reducing proteinaceous soils or stains from a surface by the step of contacting a detergent composition according to either the first or second aspect of the invention with a surface having proteinaceous stains thereon. Suitable conditions to effect the removal are employed in the method.

The method is preferably carried out in an automatic washing machine such as a laundry washing machine or an automatic dishwashing machine, especially the latter.

Surprisingly, it has been found that the detergent compositions according to the present invention exhibit good efficacy in removal of proteinaceous stains, even, in alkaline detergents. Furthermore when used in automatic dishwashing compositions good performance is also found on bleachable stain removal and/or on the inhibition of the formation of filming and/or spotting e.g. on glassware. Additionally the compositions of the second aspect of the invention exhibit good stability of ingredients which assists in providing good performance properties.

Unless stated otherwise, all amounts herein are given as the percentage by weight of active ingredient based upon the weight of the total composition.

The term 'substantially free of' as used herein means less than 0.5% wt of the material in question based on the total weight of that material in the detergent composition.

By the term 'water soluble or water dispersible packaging' as used herein is meant a package which at least partially dissolves in water or disperses in water at 20° C. within 10 minutes to allow for egress of the contents of the package into the surrounding water.

DETAILED DESCRIPTION

The present invention will now be described in further detail.

The detergent compositions of the present invention comprise a subtilisin variant having the amino acid sequence set forth in SEQ ID NO 1 and the additional ingredients recited in Claim 1. One or more of each type of additional ingredient may be present in the compositions.

a) Detergent Composition

The detergent compositions of the present invention may be in any suitable form, including but not limited to; liquids, gels, pastes, granules or powder and unit dose compositions such as shaped bodies e.g. tablets rod, ball or lozenge and compositions at least partly enveloped by a water-soluble or dispersible material which may be a self-supporting body or a pouch. The shaped body may be formed of compressed powder or cast, injection moulded or extruded material. Any suitable conventional method may be used to produce the solid detergent composition e.g. tabletting of granular/particulate material or injection moulding and these processes are well know to the person skilled in the art and thus do not need to be described further here.

It is preferred that the composition is a laundry composition or a dishwashing composition and in particular an automatic dishwashing detergent composition. However in other embodiments of the present invention the composition may take the form of a hard surface cleaner such as a floor or wall cleaning composition.

Preferably the detergent compositions of the invention are alkaline, more preferably having a pH in the range of 9-12 at 1% wt solution at 20° C., most preferably 9.5-11.5. Alkaline detergent compositions are particularly effective in laundry and automatic dishwashing applications.

A unit dose detergent composition is designed to be used as a single portion of detergent composition in a single washing operation. Of course, one or more of such single portions may be used in a cleaning operation if desired.

The detergent compositions of the present invention may be made by any suitable method as well known to the person skilled in the art.

b) Subtilisin Variant Having the Amino Acid Sequence Set Forth in SEQ ID NO 1

The subtilisin variant used in the compositions of the present invention has the amino acid sequence set forth as SEQ ID NO; 1 herein;

```
                                              (SEQ ID NO; 1)
AQSVPWGISRVQAPAAHNRGLTGSGVKVAVLDTGISTHPDLNIRGG

ASFVPGEPSTQDGNGHGTHVAGTIAALNNSIGVLGVAPNAELYAVK

VLGASGMGSVSSIAQGLEWAGNNVMHVANLSLGLQAPSATLEQAVN

SATSRGVLVVAASGNSGAGSISYPARYANAMAVGATDQNNNRASFS

QYGAGLDIVAPGVNVQSTYPGSTYASLNGTSMATPHVAGAAALVKQ

KNPSWSNVQIRNHLKNTATSLGSTNLYGSGLVNAEAATR.
```

It is preferred that the subtilisin variant having the amino acid sequence set forth in SEQ ID NO 1 is used in the compositions of the inventions as an isolated variant.

It is used as a mature form comprising the aforementioned amino acid sequence.

As used herein the term 'subtilisin' refers to any member of the S8 serine protease family as described in MEROPS—the Peptidase base (Rawlings et al, MEROPS; the peptidase database, Nucleic Acids Res, 34 Database issue, D270-272, 2006 at the website merops.sanger.ac.uk/cgi-bin/merops.cgi?id=s08:action+).

The compositions of the present invention comprise an effective amount of the subtilisin variant having the amino acid sequence set forth as SEQ ID NO; 1 herein. This amount is readily determined by the person skilled in the art. Typically the compositions comprise 0.005-2% wt of the active enzyme, preferably 0.01-1.5% wt, such as 0.05 to 1% wt.

The present specification discloses the amino acid sequence of the variant subtilisin employed in the composition of the invention. The enzyme may be added in any suitable form to the compositions; liquid or granular form. The enzyme may be used in either an encapsulated or unencapsulated form using any suitable encapsulant and encapsulating method known in the art. If encapsulated then a water-soluble or water-dispersible encapsulant (at 20° C.) is preferably used The person skilled in the art can, given the benefit of the present disclosure, routinely prepare and produce the variant subtilisin polypeptide, and indeed produce further variants thereof (e.g. fusion proteins or chimeras) or introduce other sequences to facilitate cloning (e.g. restriction endonuclease recognition sites) or purification of the expressed polypeptide (e.g. N terminal histidine tag).

In particular, nucleic acid sequences encoding the variant enzyme can be prepared in non-inventive manner. This could be accomplished by de novo synthesis of oligonucleotides which can then be assembled, using standard molecular biological techniques, into a full length double stranded nucleic acid molecule encoding the variant enzyme. Oligonucleotides can be designed and then synthesized by e.g. the phosphoramidite method (Beaucage & Carruthers 1981, Tetrahedron Lett. 22, 1859) using a commercially available automated oligonucleotide synthesiser.

Alternatively, existing nucleic acid molecules encoding prior art subtilisin enzymes may be modified (e.g. by PCR or by site-directed mutagenesis) to produce molecules encoding the variant enzyme. Suitable techniques are well-known and described in, for instance, "Molecular Cloning A Laboratory Manual" third edition, Sambrook & Russell, published by Cold Spring Harbor Laboratory Press, Cold Spring Harbor, N.Y.

Once suitable nucleic acid molecules encoding the variant subtilisin have been prepared they can be introduced by sticky end ligation into suitably digested expression vectors, and the ligated, circularised recombinant construct introduced into a suitable host for expression. Numerous expression vectors are known and readily available commercially. Preferably the promoter controlling the expression of the enzyme is inducible. The host may be a mammalian cell line, but more typically will be a micro-organism. The host may be a yeast (e.g. *Pichia* sp., *Saccharomyces* sp.) or may be a bacterium or filamentous fungus. Techniques for introducing recombinant DNA into host cells are again extremely well-known (e.g. as described by Sambrook & Russell cited above) and, in brief, include transformation, transduction and electroporation. $Ca^{2+}$-mediated transformation of susceptible bacterial cells (e.g. Birnboim & Doly 1979 Nucl. Acids Res. 7. 1513-1523) is a preferred technique, being reliable and simple to perform.

In some preferred embodiments, the variant subtilisin polypeptide will comprise a signal peptide, recognised by the host in question, such that the expressed protein is secreted by the host into the periplasmic space and/or the extracellular medium, which facilitates purification of the enzyme. In preferred embodiments, the expressed polypeptide is separated from the culture medium by filtration and/or centrifugation, and may optionally be concentrated by any of several methods well-known in the art including, for example, ultrafiltration, diafiltration or tangential flow filtration. Commercial ultrafiltration products are available from e.g. Millipore, whilst diafiltration products are supplied by e.g. Pall Life Sciences (Ann Arbor, Mich.) or Sartorius AG/Vivascience (Hannover, Germany).

The purity of the enzyme preparation can be assessed by standard techniques such as SDS-PAGE analysis and protein assays (e.g. the "Bradford" or "Lowry" methods, which are both standard and well-known). Once purified, the enzyme may be freeze-dried or stored frozen at −20° C. until required.

c) Percarbonate, Persulphate and Organic Peracid Bleaches

According to one embodiment the detergent compositions of the invention contains at least one percarbonate and/or persulphate bleach in addition to the claimed subtilisin variant enzyme. The sodium and potassium salts of percarbonate and persulphate are preferred, especially the sodium salts. Mixtures of percarbonate and persulphate bleach may be used if desired.

The compositions of the invention may comprise the percarbonate or persulphate bleach in any suitable amount, preferably in an amount of from 1% wt-50% wt, such as 5% wt-40% wt, especially 10% wt-35% wt. e.g. 15% wt-30% wt.

The percarbonate or persulphate bleach may optionally be encapsulated/coated with any suitable material.

According to one aspect of the invention the detergent compositions preferably comprise at least one organic peracid bleach, preferably a perbenzoic acid and/or a per-oxycarboxylic acid in addition to the claimed subtilisin variant enzyme.

Preferably the peroxycarboxylic acid comprises monoperoxyphthalic acid, diperoxyphthalic acid, 2-octyldiperoxysuccinic acid, diperoxydodecanedicarboxylic acid, diperoxy-azelaic acid, imidoperoxycarboxylic acid or phthalimidoperhexanoic acid including derivatives and salts thereof and mixtures thereof. Especially preferred is phthalimidoperhexanoic acid (PAP) and derivatives and salts thereof.

The compositions of the invention may comprise the organic peracid in any suitable amount, preferably in an amount of from 1% wt-50% wt, such as 5% wt-40% wt, especially 10% wt-35% wt. e.g. 15% wt-30% wt.

The organic peracid may optionally be encapsulated/coated with any suitable material.

d) Aminocarboxylates

According to one aspect of the invention the detergent compositions preferably comprise at least one aminocarboxylate builders in addition to the claimed subtilisin variant enzyme. Mixtures of such compounds may also be used.

Preferred examples of aminocarboxylates builders for use in the compositions of the present invention acid based compounds which may be used according to the invention include MGDA (methyl-glycine-diacetic acid, and salts and derivatives thereof) and GLDA (glutamic-N,N-diacetic acid and salts and derivatives thereof) and mixtures of MGDA and GLDA.

Other suitable builders are described in U.S. Pat. No. 6,426,229 and are incorporated by reference herein. Particular suitable builders include; for example, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl)aspartic acid (SEAS), N-(2-sulfomethyl)glutamic acid (SMGL), N-(2-sulfoethyl)glutamic acid (SEGL), N-methyliminodiacetic acid (MIDA), α-alanine-N,N-diacetic acid (α-ALDA), β-alanine-N,N-diacetic acid (β-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts or ammonium salts thereof.

Conventional amounts of the aminocarboxylates builders are used in the detergent compositions of the present invention, typically in the range of from 20% wt to 80% wt, such as 25 or 30% wt to 60 or 70% wt.

e) Sulphonated Polymers

Preferred examples of the sulphonated polymers include copolymers of $CH_2=CR^1-CR^2R^3-O-C_4H_3R^4-SO_3X$ wherein $R^1$, $R^2$, $R^3$, $R^4$ are independently 1 to 6 carbon alkyl or hydrogen, and X is hydrogen or alkali with any suitable other monomer units including modified acrylic, fumaric, maleic, itaconic, aconitic, mesaconic, citraconic and methylenemalonic acid or their salts, maleic anhydride, acrylamide, alkylene, vinylmethyl ether, styrene and any mixtures thereof. Other suitable sulfonated monomers for incorporation in sulfonated (co)polymers are 2-acrylamido-2-methyl-1-propanesulphonic acid, 2-methacrylamido-2-methyl-1-propanesulphonic acid, 3-methacrylamido-2-hydroxy-propanesulphonic acid, allysulphonic acid, methallysulphonic acid, 2-hydroxy-3-(2-propenyloxy)propanesulphonic acid, 2-methyl-2-propenen-1-sulphonic acid, styrenesulphonic acid, vinylsulphonic acid, 3-sulphopropyl acrylate, 3-sulphopropylmethacrylate, sulphomethylacrylamide, sulphomethylmethacrylamide and water soluble salts thereof. Suitable sulphonated polymers are also described in U.S. Pat. No. 5,308,532 and in WO 2005/090541.

It is especially preferred that the sulphonated polymer comprises monomers of a carboxylic acid and a sulphonated monomer, especially acrylic acid and/or 2-acrylamido-2-methyl-1-propanesulphonic acid (AMPS). It is most preferred that the sulphonated polymer is a copolymer of acrylic acid and AMPS, especially in a weight ratio (of the monomers of 50:50 to 90:10, such as 70:30 to 80:20.

When a sulphonated polymer is present, it is preferably present in the detergent composition in an amount of at least 0.5 wt %, preferably at least 1 wt %, more preferably at least 2 wt %, and most preferably at least 5 wt %, up to 40 wt %, preferably up to 30 wt %, more preferably up to 20 wt %, and most preferably up to 15 wt %.

Organophosphonic Acids

Organophosphonic acids are often used as corrosion inhibitors. Diphosphonic acids and their salts are preferred according to the present invention with the tetrasodium and disodium salts being especially preferred. 1, hydroxy, ethylidene 1,1-diphosphonic acid (HEDP) and its tetrasodium or disodium salts is especially preferred.

The organophosphonic acid is preferably used in an amount of from 0.05 to 5% wt, such as 0.01 to 2% wt.

g) Water Soluble or Water Dispersible Package

According to the second aspect of the invention the detergent compositions are at least partially enveloped by a water soluble or water dispersible package. Thus this is a unit dose detergent composition intended to be consumed in a single washing operation. The water soluble or water dispersible packaging material preferably fully envelopes the detergent composition.

It is preferred according to one embodiment of the invention that the water soluble or water dispersible package comprises a plurality of compartments, typically 2 to 5 compartments. This has the advantage of allowing incompatible ingredients of the overall formulation to be physically separated from each other which can increase the stability of the overall composition. For example bleach compounds and bleach sensitive ingredients such as colourants, perfumes and/or enzymes can be separated.

In this aspect of the invention the detergent compositions may be of any formulation including those of the first aspect of the invention (however they are not limited to only the compositions of the first aspect). Thus according the second aspect of the invention the detergent compositions may comprise any of the ingredients recited herein although those of the first aspect are preferred.

The water soluble or water dispersible package may be of any suitable form e.g. pouch or a self-supporting body such as one with a substantially planar base and upstanding side walls which container is typically closed with a film lid. In some embodiments of the invention it may comprise a partially pre-formed container. Preferred examples of such containers include gelatin capsules, such as those employed in medicament applications. When gelatin is used it will be appreciated that the formulation and the physical nature of the gelatin may wary widely.

For example the gelatin may be a hard gelatin or a soft gelatin (having a plasticiser component such as water, glycerine, mono-propylene glycol or polyethylene glycol).

As stated above the water soluble or water dispersible package may be in the form of a self supporting body. Preferably this is a self-supporting body with a substantially planar base and upstanding side walls which is typically closed with a film lid. Such a body may be of any shape but will typically be of a substantially square or rectangular cross section. The package may also not be in the form of a walled container but instead a shape, which is substantially self supporting (optionally with pores/apertures). The self supporting body preferably comprises a matrix. The matrix may be formed of the material used for the film of the package or alternatively the matrix may comprise a second material. Preferred matrix forming materials include gelatin, especially in an admixture with glycerine, optionally with water. A further preferred matrix forming material is polyethylene glycol (PEG) having a molecular mass of 3000 or above, e.g. such as 6000, 8000, 20000, 35000 or 8 million.

Generally the package has a maximum dimension in at least one plane of between 5 and 60 mm, preferably between 10 and 50 mm, such as between 20 and 45 mm. It will be appreciated that the size of the package will vary in accordance with desires of the unit dose detergent product formulator and the intended use of the package. It is especially preferred that the package has this dimension in at least two planes and most preferably in three planes.

The package may be formed by any suitable method, for example the method described in WO 2004/081161 which method is incorporated by reference herein. If the package is a self supporting body produced by injection moulding then it can be made according to the process disclosed in EP-A-1232100 which is incorporated by reference herein.

When the package comprising the detergent composition is a flexible pouch, the method may comprise the step of enveloping the detergent composition with at least one sheet of the material used to form the packaging, especially a flexible sheet of the packaging material. The detergent composition may be in any suitable form when it is enveloped such as a solid (including a powder), slurry or gel form. If it is in a solid form particulate/granular or tablet forms are preferred.

One way of producing the water soluble or water dispersible package in the form of a pouch containing the detergent composition is to form a cavity in a first sheet of the packaging material used to form the pouch and add the detergent composition thereto prior to the packaging material being sealed to produce the water soluble or water dispersible packaging pouch. The package may be sealed by the addition of a second sheet of the packaging material over the cavity containing the detergent composition and sealing it to the first sheet of the packaging material. The first and second sheets of the packaging material may comprise the same or different water soluble or dispersible packaging material however the two sheets preferably comprise the same packaging material.

The water soluble or water dispersible package of the invention may be formed by any suitable conventional method, for example, vacuum forming, thermoforming or injection moulding depending upon the type of packaging to be produced e.g. flexible pouch or self supporting container. For example, in a thermoforming process the film may be drawn down or blown down into a mould. Thus, for example, the film is heated to the thermoforming temperature using a thermoforming heater plate assembly, and then drawn down under vacuum or blown down under pressure into the mould. Plug-assisted thermoforming and pre-stretching the film, for example by blowing the film away from the mould before thermoforming, may, if desired, be used. One skilled in the art can choose an appropriate temperature, pressure or vacuum and dwell time to achieve an appropriate package. The amount of vacuum or pressure and the thermoforming temperature used depend on the thickness and porosity of the film and on the polymer or mixture of polymers being used. Thermoforming of PVOH films is known and described in, for example, WO 00/55045.

Polyvinyl alcohol is one suitable material from which to form the water dispersible or water soluble package (see further details below). A suitable forming temperature for PVOH or ethoxylated PVOH is, for example, from 90 to 130° C., especially 90 to 120° C. A suitable forming pressure is, for example, 69 to 138 kPa (10 to 20 p.s.i.), especially 83 to 117 kPa (12 to 17 p.s.i.). A suitable forming vacuum is 0 to 4 kPa (0 to 40 mbar), especially 0 to 2 kPa (0 to 20 mbar). A suitable dwell time is, for example, 0.4 to 2.5 seconds, especially 2 to 2.5 seconds.

The packaging material used to produce the water soluble or water dispersible package is preferably polymeric. Preferably the water soluble or water dispersible polymeric material is selected from polyvinyl alcohol, celluloses (including cellulose derivatives), starches, gelatine, polyglycolides, gelatine and polylactides copolymers or a mixture or co-polymer thereof. Polyvinyl alcohol is especially preferred as the packaging material. Preferred cellulose derivatives include hydroxyproppyl cellulose ether (HMPC). The polymeric material may be a photopolymer or a co-polymer of any suitable monomers such as those of the aforementioned types.

The water soluble or water dispersible polymeric material may, for example, be formed of a film. The film may be a single film, or a laminated film as disclosed in GB-A-2,244, 258. While a single film may have pinholes, the two or more layers in a laminate are unlikely to have pinholes which coincide.

The thickness of at least one, and preferably all, of the external walls of the water soluble or water dispersible package may be up to 2 mm, more preferably up to 1 mm, more preferably 10 to 300 μm, more preferably 20 to 200 μm, especially 25 to 160 μm, more especially 30 to 150 μm and most especially 30 to 150 μm.

The packaging material, e.g. film, may be produced by any process, for example by extrusion and blowing or by casting. The film may be unoriented, monoaxially oriented or biaxially oriented. If the layers in the film are oriented, they usually have the same orientation, although their planes of orientation may be different if desired. The layers in a laminate may be the same or different. Thus they may each comprise the same polymer or a different polymer.

Examples of the water-soluble or dispersible polymeric material which may be used in a single layer film or in one or more layers of a laminate or which may be used for injection moulding or blow moulding are poly(vinyl alcohol) (PVOH), cellulose derivatives such as hydroxypropyl methyl cellulose (HPMC) and gelatin. An example of a suitable PVOH is ethoxylated PVOH. The PVOH may be partially or fully alcoholised or hydrolysed. For example it may be from 40 to 100%, preferably from 70 to 92%, more preferably about 88% or about 92%, alcoholised or hydrolysed. The degree of hydrolysis is known to influence the temperature at which the PVOH starts to dissolve in water. 88% hydrolysis corresponds to a film soluble in cold (i.e. room temperature) water, whereas 92% hydrolysis corresponds to a film soluble in warm water. Therefore the water soluble characteristics of the film can be controlled.

Other Optional Ingredients

In addition to the ingredients specified above the compositions of the invention most preferably also comprise one or more surfactants to aid with cleansing.

If a surfactant is present it may be any of nonionic, anionic, cationic, amphoteric or zwitterionic surface active agents or mixtures thereof. Many such suitable surfactants are described in Kirk Othmer's Encyclopedia of Chemical Technology, 3rd Ed., Vol. 22, pp. 360-379, "Surfactants and Detersive Systems", incorporated by reference herein. In general, bleach-stable surfactants are preferred according to the present invention.

For automatic dishwashing compositions according to the present invention non-ionic surfactants are especially preferred. For laundry and other cleaning applications other surfactants such as anionic surfactants are preferably included and suitable types are well known in the art.

A preferred class of nonionic surfactants is ethoxylated non-ionic surfactants prepared by the reaction of a monohydroxy alkanol or alkylphenol with 6 to 20 carbon atoms. Preferably the surfactants have at least 12 moles particularly preferred at least 16 moles, and still more preferred at least 20 moles, such as at least 25 moles of ethylene oxide per mole of alcohol or alkylphenol.

Particularly preferred non-ionic surfactants are the non-ionics from a linear chain fatty alcohol with 16-20 carbon atoms and at least 12 moles, particularly preferred at least 16 and still more preferred at least 20 moles, of ethylene oxide per mole of alcohol.

According to one embodiment of the invention, the non-ionic surfactants additionally may comprise propylene oxide units in the molecule. Preferably these PO units constitute up to 25% by weight, preferably up to 20% by weight and still more preferably up to 15% by weight of the overall molecular weight of the non-ionic surfactant.

Surfactants which are ethoxylated mono-hydroxy alkanols or alkylphenols, which additionally comprises polyoxyethylene-polyoxypropylene block copolymer units may be used. The alcohol or alkylphenol portion of such surfactants constitutes more than 30%, preferably more than 50%, more preferably more than 70% by weight of the overall molecular weight of the non-ionic surfactant. Another class of suitable non-ionic surfactants includes reverse block copolymers of polyoxyethylene and polyoxypropylene and block copolymers of polyoxyethylene and polyoxypropylene initiated with trimethylolpropane. Another preferred class of nonionic surfactant can be described by the formula:

where $R^1$ represents a linear or branched chain aliphatic hydrocarbon group with 4-18 carbon atoms or mixtures thereof, $R^2$ represents a linear or branched chain aliphatic hydrocarbon rest with 2-26 carbon atoms or mixtures thereof, x is a value between 0.5 and 1.5 and y is a value of at least 15.

Another group of preferred nonionic surfactants are the end-capped polyoxyalkylated non-ionics of formula:

where $R^1$ and $R^2$ represent linear or branched chain, saturated or unsaturated, aliphatic or aromatic hydrocarbon groups with 1-30 carbon atoms, $R^3$ represents a hydrogen atom or a methyl, ethyl, n-propyl, iso-propyl, n-butyl, 2-butyl or 2-methyl-2-butyl group, x is a value between 1 and 30 and, k and j are values between 1 and 12, preferably between 1 and 5. When the value of x is >2 each $R^3$ in the formula above can be different. $R^1$ and $R^2$ are preferably linear or branched chain, saturated or unsaturated, aliphatic or aromatic hydrocarbon groups with 6-22 carbon atoms, where group with 8 to 18 carbon atoms are particularly preferred. For the group $R^3H$, methyl or ethyl is particularly preferred. Particularly preferred values for x are comprised between 1 and 20, preferably between 6 and 15.

As described above, in case x>2, each $R^3$ in the formula can be different. For instance, when x=3, the group $R^3$ could be chosen to build ethylene oxide ($R^3$=H) or propylene oxide ($R^3$=methyl) units which can be used in every single order for instance (PO)(EO)(EO), (EO)(PO)(EO), (EO)(EO)(PO), (EO)(EO)(EO), (PO)(EO)(PO), (PO)(PO)(EO) and (PO)(PO)(PO). The value 3 for x is only an example and bigger values can be chosen whereby a higher number of variations of (EO) or (PO) units would arise.

Particularly preferred end-capped polyoxyalkylated alcohols of the above formula are those where k=1 and j=1 originating molecules of simplified formula:

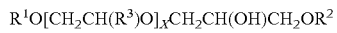

$R^1O[CH_2CH(R^3)O]_xCH_2CH(OH)CH_2OR^2$

The use of mixtures of different nonionic surfactants is suitable in the context of the present invention for instance mixtures of alkoxylated alcohols and hydroxy group containing alkoxylated alcohols.

Other suitable surfactants are disclosed in WO 95/01416, to the contents of which express reference is hereby made.

Preferably the non-ionic surfactants are present in the detergent compositions of the invention in an amount of from 0.1% wt to 20% wt, more preferably 0.5% wt to 15% wt, such as 1 to 10% wt.

The detergent compositions of invention may comprise additional bleaching compounds to those forming part of the first aspect of the invention. Any type of additional bleaching compound conventionally used in detergent compositions may be used.

This additional bleaching compound preferably comprises at least one inorganic peroxide or a chlorine based bleach including derivatives and salts thereof or mixtures thereof but excluding the bleaches mentioned according to the first aspect of the invention. Preferably the at least one inorganic peroxide comprises a perborate and/or hydrogen peroxide including derivatives and salts thereof and mixtures thereof. The sodium and potassium salts of these inorganic peroxides being most preferred, especially the sodium salts.

The detergent compositions of the invention may also optionally comprise a non-aminocarboxylate builder in addition to any aminocarboxylates builders and phosphonate builders present in the compositions. If any such builder is present it may be either a phosphorous-containing builder or a phosphorous-free builder as desired.

If phosphorous-containing builders are also used in the detergent compositions of the inventions (whether or not any phosphonates are present) it is preferred that mono-phosphates, di-phosphates, tri-polyphosphates or oligomeric-poylphosphates are used. The alkali metal salts of these compounds are preferred, in particular the sodium salts. An especially preferred builder is sodium tripolyphosphate (STPP). Conventional amounts of the phosphorous-containing builders may be used in the solid detergent compositions, typically in the range of from 15% wt to 80% wt, such as 20% wt to 75% wt, more preferably 25% wt to 60% wt.

For phosphorous-free builders suitable examples include succinate based builders. The terms 'succinate based compound' and 'succinic acid based compound' are used interchangeably herein. Preferred succinate compounds are described in U.S. Pat. No. 5,977,053 and have the formula;

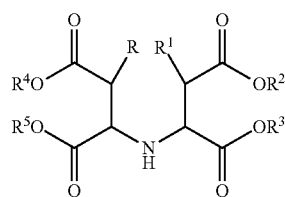

in which R, $R^1$, independently of one another, denote H or OH, $R^2$, $R^3$, $R^4$, $R^5$, independently of one another, denote a cation, hydrogen, alkali metal ions and ammonium ions, ammonium ions having the general formula $R^6 R^7 R^8 R^9 N+$ and $R^6$, $R^7$, $R^8$, $R^9$, independently of one another, denoting hydrogen, alkyl radicals having 1 to 12 C atoms or hydroxyl-substituted alkyl radicals having 2 to 3 C atoms. Preferred examples include tetrasodium imminosuccinate. Iminodisuccinic acid (IDS) and (hydroxy)iminodisuccinic acid (HIDS) and alkali metal salts or ammonium salts thereof are especially preferred succinate based builder salts.

The phosphorous-free builder may also or alternatively comprise non-polymeric organic molecules with carboxylic group(s). Builder compounds which are organic molecules containing carboxylic groups include citric acid, fumaric acid, tartaric acid, maleic acid, lactic acid and salts thereof. In particular the alkali or alkaline earth metal salts of these organic compounds may be used, and especially the sodium salts. An especially preferred phosphorous-free builder is sodium citrate. Such polycarboxylates which comprise two carboxyl groups include, for example, water-soluble salts of, malonic acid, (ethylenedioxy)diacetic acid, maleic acid, diglycolic acid, tartaric acid, tartronic acid and fumaric acid. Such polycarboxylates which contain three carboxyl groups include, for example, water-soluble citrate. Correspondingly, a suitable hydroxycarboxylic acid is, for example, citric acid.

Conventional amounts of these phosphorous free builders may be used in the solid detergent compositions, typically in the range of from 20% wt to 80% wt, such as 25 or 30% wt to 60 or 70% wt.

Preferably the total amount of builder present in the compositions (including any organic peracid and/or aminocarboxylate builder) is at least 20 wt %, and most preferably at least 25 wt %, preferably in an amount of up to 70 wt %, preferably up to 65 wt %, more preferably up to 60 wt %. The actual amount used in the compositions will depend upon the nature of the builder used. If desired a combination of phosphorous-containing and phosphorous-free builders may be used.

When the compositions comprise a bleach, in particular a percarbonate or persulphate bleach, they may preferably comprise one or more bleach activators or bleach catalysts depending upon the nature of the bleaching compound. Any suitable bleach activator may be included for example TAED. Any suitable bleach catalyst may be used for example manganese acetate or dinuclear manganese complexes such as those described in EP-A-1,741,774. Conventional amounts may be used e.g. in amounts of from 0.01 to 10 wt %, more preferred of from 0.1 to 8 wt % and most preferred of from 0.5 to 5 wt % based on the weight of the total composition.

Any type of enzyme typically used in detergent compositions may be included in the compositions of the present invention in addition to the claimed Bacillus sp. subtilisin variant. It is preferred that this additional enzyme is selected from other proteases, lipases, amylases, cellulases and peroxidases, with other proteases and amylases being most preferred. It is most preferred that protease and/or amylase enzymes are included in the compositions according to the invention as such enzymes are especially effective for example in dishwashing detergent compositions. Any suitable species of these enzymes may be used as desired. Conventional amounts of such enzymes may be used.

The compositions according to the invention may also comprise a source of acidity or a source of alkalinity, to obtain the desired pH, on dissolution, especially if the composition is to be used in an automatic dishwashing application. Preferred silicates are sodium silicates such as sodium disilicate, sodium metasilicate and crystalline phyllosilicates. A source of acidity may suitably be any suitable acidic compound for example a polycarboxylic acid. For example a source of alkalinity may be a carbonate or bicarbonate (such as the alkali metal or alkaline earth metal salts). A source of alkalinity may suitably be any suitable basic compound for example any salt of a strong base and a weak acid. When an alkaline composition is desired silicates are amongst the suitable sources of alkalinity. Conventional amounts of the alkalinity or acidity source may be used.

The detergent compositions may comprise one or more anti-corrosion agents, especially when the detergent compositions are for use in automatic dishwashing operations. These anti-corrosion agents may provide benefits against corrosion of glass and/or metal and the term encompasses agents that are intended to prevent or reduce the tarnishing of non-ferrous metals, in particular of silver and copper. In many detergent compositions according to the present invention it may be desirable to include more than one type of anti-corrosion agent to provide protection against corrosion of glass and metals.

It is known to include a source of multivalent ions in detergent compositions, and in particular in automatic dishwashing compositions, for anti-corrosion benefits. For example, multivalent ions and especially zinc, bismuth and/or manganese ions have been included for their ability to inhibit such corrosion. Organic and inorganic redox-active substances which are known as suitable for use as silver/copper corrosion inhibitors are mentioned in WO 94/26860 and WO 94/26859. Suitable inorganic redox-active substances are, for example, metal salts and/or metal complexes chosen from the group consisting of zinc, bismuth, manganese, titanium, zirconium, hafnium, vanadium, cobalt and cerium salts and/or complexes, the metals being in one of the oxidation states II, III, IV, V or VI. Particularly suitable metal salts and/or metal complexes are chosen from the group consisting of $MnSO_4$, Mn(II) citrate, Mn(II) stearate, Mn(II) acetylacetonate, Mn(II) [1-hydroxyethane-1,1-diphosphonate], $V_2O_5$, $V_2O_4$, $VO_2$, $TiOSO_4$, $K_2TiF_6$, $K_2ZrF_6$, $CoSO_4$, $Co(NO_3)_2$ and $Ce(NO_3)_3$. Any suitable source of multivalent ions may be used, with the source preferably being chosen from sulphates, carbonates, acetates, gluconates and metal-protein compounds. Zinc salts are specially preferred corrosion inhibitors.

Preferred silver/copper anti-corrosion agents are benzotriazole (BTA) or bis-benzotriazole and substituted derivatives thereof. Other suitable agents are organic and/or inorganic redox-active substances and paraffin oil. Benzotriazole derivatives are those compounds in which the available substitution sites on the aromatic ring are partially or completely substituted. Suitable substituents are linear or branch-chain $C_{1-20}$ alkyl groups and hydroxyl, thio, phenyl or halogen such as fluorine, chlorine, bromine and iodine. A preferred substituted benzotriazole is tolyltriazole.

Therefore, an especially preferred optional ingredient according to the present invention is a source of multivalent ions such as those mentioned in the immediately preceding paragraphs and in particular compounds comprising zinc, bismuth and/or manganese ions and/or benzotriazole, including substituted benzotriazoles. In particular a source of zinc ions and unsubstituted benzotriazole are preferred as anti-corrosion agents and a mixture of these two ingredients is especially preferred according to the invention.

Any conventional amount of the anti-corrosion agents may be included in the solid detergent compositions of the invention. However, it is preferred that they are present in an total amount of from 0.01% wt to 5% wt, preferably 0.05% wt to 3% wt, more preferably 0.1 to 2.5% wt, such as 0.2% wt to 2% wt based on the total weight of the composition.

If more than one anti-corrosion agent is used, the individual amounts may be within the preceding amounts given but the preferred total amounts still apply.

The detergent composition may also comprise one or more foam control agents. Suitable foam control agents for this purpose are all those conventionally used in this field, such as, for example, silicones and their derivatives and paraffin oil. The foam control agents are preferably present in the composition in amounts of 0.5% by weight or less of the total weight of the composition.

If the detergent composition is in the form of a shaped body e.g. a tablet then a conventional amount of a binder material may be included in that region. Any conventional binders may be used, typically in an amount of up to 10% wt, more preferably in an amount of up to 5% wt in that distinct region. Suitable binders include polyethylene glycols and/or glycerol.

The detergent compositions of the invention may also comprise minor, conventional, amounts of preservatives, dyes, colurants and perfume as desired. Such ingredients are typically present in amounts of up to 2% wt.

The invention also provides a method of removing or reducing proteinaceous soils or stains from a surface by the step of contacting a detergent composition according to either the first or second aspect of the invention with a surface having proteinaceous stains thereon. Suitable conditions to effect the removal are employed in the method and will typically involve contact under aqueous conditions and usually at a temperature in the range of from 15-70° C., such as 30-70° C.

The method is preferably carried out in an automatic washing machine such as a laundry washing machine or an automatic dishwashing machine, especially the latter.

The invention is further described with reference to the following non-limiting Examples. Further examples within the scope of the invention will be apparent to the person skilled in the art.

EXAMPLES

Example 1

The subtilisin variant having the amino acid sequence set forth in SEQ ID NO 1, was included in a 21 gram multi-layer automatic dishwashing tablet with a pill contained in a cavity on the upper layer, the tablet having the composition as shown in table 1. The weights for lower layer 1, top layer 2 and pill are expressed as % wt based upon the total weight thereof. Layer 1 represents about 65.42% wt of the tablet, layer 2 represents about 28.03% wt of the tablet and the pill represents about 6.55% wt of the tablet.

The tablet was produced by compaction of the granular formulations to produce the relevant layers and the pill. The tablet was wrapped in a water soluble PVOH wrapper. The granular formulations were produced by spray drying the relevant ingredients together.

TABLE 1 multilayer automatic dishwashing tablet comprising subtilisin variant having the amino acid sequence set forth in SEQ ID NO 1.

| Ingredient | Layer 1 (lower) | Layer 2 (top) | Pill |
|---|---|---|---|
| Sodium percarbonate | 20.00 | — | — |
| Sodium tripolyphosphate | 46.45 | 52.00 | — |

TABLE 1-continued multilayer automatic dishwashing tablet comprising subtilisin variant having the amino acid sequence set forth in SEQ ID NO 1.

| Ingredient | Layer 1 (lower) | Layer 2 (top) | Pill |
|---|---|---|---|
| Sodium bicarbonate | — | 0.75 | 40.78 |
| Sodium carbonate | 20.45 | 21.30 | 5.50 |
| Polyethylene glycol 1500 | 1.25 | 2.10 | 1.00 |
| Polyethylene glycol 6000 | 3.50 | 1.50 | 6.00 |
| Tetrasodium salt of HEDP | 0.30 | — | — |
| Sulphonated polymer (Acusol 588G)*[1] | 3.00 | 4.10 | — |
| TAED | — | 11.00 | — |
| Amylase | — | 2.04 | — |
| subtilisin variant having the amino acid sequence set forth in SEQ ID NO 1 | — | 3.49 | 4.72 |
| Citric acid anhydrous | — | — | 16.40 |
| Magnesium stearate | — | — | 0.30 |
| Dye | — | 0.04 | — |
| C16-18 25 EO nonionic surfactant | 4.95 | — | — |
| Tolyltriazole | — | 1.10 | — |
| Microcrystalline cellulose | — | — | 25.00 |
| Perfume | — | 0.38 | 0.30 |
| Glycerol | 0.10 | 0.20 | — |

*[1]Available ex Rohm and Haas, a copolymer of Acrylic acid and AMPS.

The wrapped tablet was placed in the dispenser draw of a Miele G 651 SC Plus dishwasher loaded with kitchen items as detailed below. A 50° C. normal wash cycle was run using a water hardness of 21 German hardness to assess the proteinaceous stain removal ability of the detergent tablet.

The kitchenware used in the dishwasher was pre-soiled with three types of proteinaceous stains; egg yolk, Egg/milk and minced meat according to the IKW test method for proteinaceous stains (IKW, Germany test method for ascertaining the cleaning performance of dishwasher detergents (SÖFW journal 11/99). The proteinaceous stain removal ability of the tablet was assessed using the above method. Good proteinaceous stain removal was obtained.

As a comparison the subtilisin variant having the amino acid sequence set forth in SEQ ID NO 1 was replaced in the above formulation by an alternative commercially available protease, and the test repeated using the same test method and materials. Improved proteinaceous stain removal was found according to the automatic dishwashing composition of the invention.

Alternatively the granular formulations used to produce layer 1, layer 2 and the pill of the above example may be used in granular form in a multi-compartment water soluble package such as a poly vinyl alcohol multi-compartment pouch or free standing capsule. In such an arrangement each formulation would be contained within a separate compartment and preferably incompatible materials would be separated.

Example 2

The subtilisin variant having the amino acid sequence set forth in SEQ ID NO 1 may also be included in a 21 gram multi-layer automatic dishwashing tablet as according to Example 1 but where the builder system comprises MGDA and/or GLDA as shown in Table 2.

TABLE 2

MGDA-containing automatic dishwashing tablet

| Ingredient | Layer 1 (lower) | Layer 2 (top) | Pill |
|---|---|---|---|
| PAP | 10.00 | — | — |
| MGDA | 55.45 | 50.00 | — |
| Sodium bicarbonate | — | 1.75 | 40.78 |
| Sodium carbonate | 21.45 | 22.30 | 5.50 |
| Polyethylene glycol 1500 | 1.25 | 2.10 | 1.00 |
| Polyethylene glycol 6000 | 3.50 | 1.50 | 6.00 |
| Tetrasodium salt of HEDP | 0.30 | — | — |
| Sulphonated polymer (Acusol 588G)*[1] | 3.00 | 4.10 | — |
| TAED | — | 11.00 | — |
| Amylase | — | 2.04 | — |
| subtilisin variant having the amino acid sequence set forth in SEQ ID NO 1 | — | 3.49 | 4.72 |
| Citric acid anhydrous | — | — | 16.40 |
| Magnesium stearate | — | — | 0.30 |
| Dye | — | 0.04 | — |
| C16-18 25 EO nonionic surfactant | 4.95 | — | — |
| Tolyltriazole | — | 1.10 | — |
| Microcrystalline cellulose | — | — | 25.00 |
| Perfume | — | 0.38 | 0.30 |
| Glycerol | 0.10 | 0.20 | — |

The invention claimed is:

1. A detergent composition comprising:
   a subtilisin variant having the amino acid sequence set forth in SEQ ID NO 1 present in an amount of from 0.005 wt% to 2 wt%,
   at least one bleach selected from percarbonates, persulphates and organic peracids present in an amount of from 1 wt% to 50 wt%,
   at least one aminocarboxylate present in an amount of from 20 wt% to 80 wt%,
   at least one sulphonated polymer, present in an amount of at least 0.5 wt% to 15 wt%, and
   at least one organophosphonic acids or salts thereof, and mixtures thereof, present in an amount of from 0.05 wt% to 5 wt%,
   wherein the detergent composition is an automatic dishwashing detergent composition,
   wherein the detergent composition is in the form of a multilayer tablet with a pill contained in a cavity in the topmost layer,
   wherein the detergent composition is at least partially enveloped in a water soluble or water dispersible package, and
   wherein the subtilisin variant is present in the pill and at least one layer of the multilayer tablet.

2. The detergent composition according to claim 1, wherein the percarbonate or persulphate bleach comprises sodium or potassium percarbonate or persulphate.

3. The detergent composition according to claim 1, wherein the organic peracid comprises a perbenzoic acid and/or a peroxycarboxylic acid.

4. The detergent composition according to claim 3, wherein the peroxycarboxylic acid comprises monoperoxyphthalic acid, diperoxyphthalic acid, 2-octyldiperoxysuccinic acid, diperoxydodecanedicarboxylic acid, diperoxy-azelaic acid, imidoperoxycarboxylic acid or phthalimidoperhexanoic acid including derivatives and salts thereof and mixtures thereof.

5. The detergent composition according to claim 4, wherein the peroxycarboxylic acid comprises phthalimidoperhexanoic acid (PAP) or derivatives or salts thereof.

6. The detergent composition according to claim 1, wherein the aminocarboxylate comprises methyl-glycinediacetic acid, glutamic-N,N-diacetic acid, and salts or derivatives and mixtures thereof.

7. The detergent composition according to claim 1, wherein the sulphonated polymer comprises monomers of a carboxylic acid or a salt thereof and a sulphonated monomer.

8. The detergent composition according to claim 1, wherein the organophosphonic acids comprises HEDP or salts thereof.

9. The detergent composition according to claim 1, wherein the composition further comprises surfactant.

10. The detergent composition according to claim 1, wherein the detergent composition is fully enveloped by the water soluble or water dispersible package.

11. The detergent composition according to claim 1, wherein the water soluble or water dispersible package has a plurality of compartments.

12. The detergent composition according to claim 1, wherein the water soluble or water dispersible package comprises polymeric packaging material.

13. The detergent composition according to claim 12, wherein the polymeric packaging material is selected from polyvinyl alcohol, celluloses and cellulose derivatives, starches, gelatine, polyglycolides, gelatine and polylactides copolymers or a mixture or co-polymer thereof.

14. A method of removing or reducing proteinaceous soils or stains from a surface by the step of:
   contacting a detergent composition according to claim 1 with a surface having proteinaceous stains thereon.

15. The method according to claim 14, wherein the method is carried out in an automatic washing machine.

16. The method according to claim 15, wherein the automatic washing machine is an automatic dishwashing machine.

17. A detergent composition in the form of a bilayer tablet with a pill contained in a cavity in the second layer consisting of:
   the first layer consisting of:
      10 wt% phthalimidoperhexanoic acid;
      55.45 wt% methyl-glycine-diacetic acid;
      21.45 wt% sodium carbonate;
      1.25 wt% polyethylene glycol 1500;
      3.50 wt% polyethylene glycol 6000;
      0.30 wt% tetrasodium salt of 1-hydroxy-ethylidene 1,1-diphosphoric acid;
      3 wt% sulfonated polymer;
      4.95 wt% nonionic surfactant; and
      0.10 wt% glycerol;
   the second layer consisting of:
      50 wt% methyl-glycine-diacetic acid;
      1.75 wt% sodium bicarbonate;
      22.30 wt% sodium carbonate;
      2.10 wt% polyethylene glycol 1500;
      1.50 wt% polyethylene glycol 6000;
      4.10 wt% sulfonated polymer;
      11 wt% TAED;
      2.04 wt% amylase;
      3.49 wt% subtilisin variant having the amino acid sequence set forth in SEQ ID NO 1;
      0.04 wt% dye;
      1.10 wt% tolyltriazole;
      0.04 wt% perfume; and
      0.20 wt% glycerol; and
   the pill consisting of:
      40.78 wt% sodium bicarbonate;
      5.50 wt% polyethylene glycol 1500;
      1 wt% polyethylene glycol 6000;
      4.72 wt% subtilisin variant having the amino acid sequence set forth in SEQ ID NO 1;
      16.40 wt% citric acid;
      0.30 wt% magnesium stearate;
      25 wt% microcrystalline cellulose; and
      0.30 wt% perfume;
   wherein the detergent composition is an automatic dishwashing detergent composition.

* * * * *